(12) United States Patent
Balocco et al.

(10) Patent No.: US 11,064,972 B2
(45) Date of Patent: Jul. 20, 2021

(54) SYSTEMS AND METHODS FOR DETECTING AND DISPLAYING BODY LUMEN BIFURCATIONS

(75) Inventors: Simone Balocco, Badalona (ES); Marina Alberti, Barcelona (ES); Carlo Gatta, Barcelona (ES); Francesco Ciompi, Barcelona (ES); Oriol Pujol, Barcelona (ES); Xavier Carrillo, Badalona (ES); Josepa Mauri Ferre, Barcelona (ES); Oriol Rodriguez, Tiana (ES); Eduard Fernandez-Nofrerias, Barcelona (ES); Petia Radeva, Sant Cugat (ES)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1743 days.

(21) Appl. No.: 13/243,571

(22) Filed: Sep. 23, 2011

(65) Prior Publication Data

US 2012/0130243 A1 May 24, 2012

Related U.S. Application Data

(60) Provisional application No. 61/510,014, filed on Jul. 20, 2011, provisional application No. 61/416,947, filed on Nov. 24, 2010.

(51) Int. Cl.
*A61B 8/12* (2006.01)
*A61B 6/00* (2006.01)
(Continued)

(52) U.S. Cl.
CPC .............. *A61B 8/12* (2013.01); *A61B 8/0891* (2013.01); *A61B 8/4461* (2013.01);
(Continued)

(58) Field of Classification Search
CPC ......... A61B 6/504; A61B 8/0891; A61B 8/12; A61B 8/14; A61B 8/445
See application file for complete search history.

(56) References Cited

U.S. PATENT DOCUMENTS 6,148,095 A * 11/2000 Prause ................... G06T 17/00
382/131
6,945,938 B2 9/2005 Grunwald
(Continued)

FOREIGN PATENT DOCUMENTS

WO      2007002685 A2     1/2007
WO   WO 2007/002685    *   1/2007 ............... A61B 8/14
(Continued)

OTHER PUBLICATIONS

Grissan et al, A new tracking system for the robust extraction of retinal vessel structure, Proceedings of the 26th Annual International Conference of the IEEE EMBS, Sep. 2004, pp. 1620-1623.*
(Continued)

*Primary Examiner* — Oommen Jacob
*Assistant Examiner* — Shahdeep Mohammed
(74) *Attorney, Agent, or Firm* — Seager, Tufte & Wickhem, LLP

(57) ABSTRACT

A method for generating an ultrasound image includes receiving a sequence of intravascular ultrasound (IVUS) data obtained as an IVUS imager moves through a body lumen; identifying at least one bifurcation of the body lumen from the sequence of IVUS data; determining a bifurcation angle between two branches of the body lumen; and displaying a longitudinal view of the body lumen using the IVUS data and incorporating the bifurcation angle to angularly align portions of the longitudinal view corresponding to the two portions of the body lumen.

12 Claims, 9 Drawing Sheets

(51) Int. Cl.
- A61B 8/14 (2006.01)
- A61B 8/08 (2006.01)
- A61B 8/00 (2006.01)
- G06T 7/33 (2017.01)

(52) U.S. Cl.
CPC .......... *A61B 8/5223* (2013.01); *A61B 8/5261* (2013.01); *A61B 8/5276* (2013.01); *A61B 8/5284* (2013.01); *G06T 7/33* (2017.01); *A61B 6/504* (2013.01); *A61B 8/14* (2013.01); *A61B 8/445* (2013.01); *G06T 2207/10116* (2013.01); *G06T 2207/10132* (2013.01); *G06T 2207/30172* (2013.01)

(56) References Cited

U.S. PATENT DOCUMENTS

| | | | |
|---|---|---|---|
| 7,306,561 | B2 | 12/2007 | Sathyanarayana |
| 7,460,716 | B2 | 12/2008 | Sathyanarayana |
| 7,623,900 | B2 * | 11/2009 | Graham ................ G06T 19/003 382/128 |
| 7,680,307 | B2 | 3/2010 | Sathyanarayana |
| 7,729,533 | B2 | 6/2010 | Sathyanarayana |
| 2002/0049375 | A1 * | 4/2002 | Strommer ............ A61B 5/0066 600/407 |
| 2004/0066958 | A1 * | 4/2004 | Chen ...................... A61B 6/466 382/128 |
| 2005/0249391 | A1 * | 11/2005 | Kimmel ................. G06T 7/143 382/128 |
| 2006/0036167 | A1 | 2/2006 | Shina |
| 2006/0100502 | A1 * | 5/2006 | Chen .................. A61B 5/02007 600/419 |
| 2006/0100522 | A1 | 5/2006 | Yuan et al. |
| 2006/0106320 | A1 | 5/2006 | Barbato |
| 2006/0173350 | A1 | 8/2006 | Yuan et al. |
| 2006/0253028 | A1 | 11/2006 | Lam et al. |
| 2007/0016054 | A1 | 1/2007 | Cao et al. |
| 2007/0038111 | A1 | 2/2007 | Rehrig et al. |
| 2007/0287914 | A1 * | 12/2007 | Cohen ...................... A61B 8/12 600/101 |
| 2008/0004530 | A1 * | 1/2008 | Feldman ............ A61B 5/02007 600/467 |
| 2008/0101674 | A1 * | 5/2008 | Begelman ............ G06K 9/3241 382/130 |
| 2009/0060298 | A1 * | 3/2009 | Weijers ................ G06T 7/0012 382/128 |
| 2009/0103794 | A1 | 4/2009 | Sathyanarayana |
| 2009/0148024 | A1 * | 6/2009 | Park ........................ G06T 7/187 382/134 |
| 2009/0270731 | A1 | 10/2009 | Sathyanarayana |
| 2010/0022880 | A1 | 1/2010 | Sathyanarayana et al. |
| 2010/0061601 | A1 * | 3/2010 | Abramoff ................. G06T 7/33 382/117 |
| 2011/0096972 | A1 | 4/2011 | Gatta et al. |
| 2011/0280366 | A1 * | 11/2011 | Maeda ................... A61B 6/032 378/8 |
| 2012/0059248 | A1 * | 3/2012 | Holsing ............... A61B 1/2676 600/424 |

FOREIGN PATENT DOCUMENTS

| | | | | |
|---|---|---|---|---|
| WO | WO 2008111070 | A2 * | 9/2008 | ................ A61B 8/12 |
| WO | WO 2011046425 | A2 * | 4/2011 | ......... G06F 19/3437 |

OTHER PUBLICATIONS

Pujol, O. et al., "Near Real-time Plaque Segmentation of IVUS," Computers in Cardiology, vol. 30, 2003, pp. 69-72.
Rifkin, R. et al., "In Defense of One-vs-All Classification," Journal of Machine Learning Research, vol. 5, 2004, pp. 101-141.
Rotger, D. et al., "Blood Detection in IVUS Images for 3D Volume of Lumen Changes Measurement Due to Different Drugs Administartion," Proceedings of the 12th International Conference on Computer Analysis of Images and Patterns, Berlin, Deidelberg, Springer-Verlag, 2007, pp. 285-292.
Shah, P. K., "Mechanisms of Plaque Vulnerability and Rupture," Journal of the American College of Cardiology, vol. 41, No. 4, Supplement S, Feb. 2003, pp. 15S-22S.
Tanabe, K. et al., "Restenosis Rates Following Bifurcation Stenting with Sirolimus-Eluting Stents for De Novo Narrowings," American Journal of Cardiology, vol. 91, Jul. 1, 2004, pp. 115-118.
Treece, G. M. et al., "Grey-Scale Gating for Freehand 3D Ultrasound," Proceedings of IEEE International Symposium on Biomedical Imaging, 2002, pp. 993-996.
Zhu, H. et al., "Retrieval of Cardiac Phrase from IVUS Sequences," Proceedings of SPIE Medical Imaging, 2003, pp. 135-146.
Alberti, M. et al., "Automatic Bifurcation Detection in Coronary IVUS Sequences," IEEE Transactions on Biomedical Engineering, vol. PP, No. 99, 2010, 16 pages.
Ciompi, F. et al., "A Meta-Learning approach to Conditional Random Fields using Error-Correcting Output Codes", IEEE International Conference on Pattern Recognition (ICPR), 2010, 4 pages.
Wahle, A. et al., "Determination of the Absolute Axial Orientation of Intracoronary Ultrasound Images in Fusion with Biplane Angiography," Computers in Cardiology, vol. 25, 1998, pp. 153-156.
International Search Report and Written of the International Patent Application No. PCT/US2011/053116 dated Mar. 9, 2012.
Cortes, C., et al., "Support-Vector Networks," Machine Learning, vol. 20, 1995, pp. 273-297.
Lemos, P. A. et al., "Unrestricted Utilization of Sirolimus-Eluting Stents Compared with Conventional Bare Stent Implantation in the 'Real World'," Circulation, vol. 109, No. 2, Jan. 20, 2004, pp. 190-195.
Kim, S. H. et al., "Long-Term Outcomes of Intravascular Ultrasound-Guided Stenting in Coronary Bifurcation Lesions," American Journal of Cardiology, vol. 106, No. 5, Sep. 1, 2010, pp. 612-618.
Van Der Waal, E. C. et al., "Intravascular Ultrasound and 3D Angle Measurements of Coronary Bifurcations," Catheterization and Cardiovascular Interventions, vol. 73, No. 7, Jun. 1, 2009, pp. 910-916.
Colombo, A. et al., "Randomized Study of the Crush Technique versus Provisional Side-Branch Stenting in True Coronary Bifurcations: the CACTUS (Coronary Bifurcations: Application of the Crushing Technique Using Sirolimus-Eluting Stents) Study," Circulation, vol. 119, No. 1, Jan. 6, 2009, pp. 71-78.
Steigen, T. K. et al., "Randomized Study on Simple versus Complex Stenting of Coronary Artery Bifurcation Lesions: the Nordic Bifurcation Study," Circulation, vol. 114, No. 18, Oct. 31, 2006, pp. 1955-1961.
Dzavik, V. et al., "Predictors of Long-Term Outcome after Crush Stenting of Coronary Bifurcation Lesions: Importance of the Bifurcation Angle," American Heart Journal, vol. 152, No. 4, Oct. 2006, pp. 762-769.
Rotger, D. et al., "ActiveVessel: A New Multimedia Workstation for Intravascular Ultrasound and Angiography Fusion," in Computers in Cardiology, Thessaloniki, 2003, pp. 65-68.
Bourantas, C. V. et al., "A Method for 3D Reconstruction of Coronary Arteries using Biplane Angiography and Intravascular Ultrasound Images," Computerized Medical Imaging and Graphics, vol. 29, No. 8, Dec. 2005, pp. 597-606.
Gatta, C. et al., "Real-Time Gating of IVUS Sequences Based on Motion Blur Analysis: Method and Quatitative Validation," Proceedings of the 13th International Conference on Medical Image Computing and Computer Assisted Intervention, vol. 2, 2010, pp. 59-67.
Ciompi, F. et al., "ECOC Random Fields for Lumen Segmentation in Radial Artery IVUS Sequences," Medical Image Computing and Computer-Assisted Intervention, vol. 12, Pt. 2, 2009, pp. 869-876.
Merle, A. B. et al., "3D Reconstruction of the Deformable Coronary Tree Skeleton from Two X-Ray Angiographic Views," Computers in Cardiology, Sep. 1998, pp. 757-760.
Ardizzone, E. et al., "Automatic Extraction of Blood Vessels, Bifurcation and End Points in the Retinal Vascular Tree," 13th International Conference on Biomedical Engineering, IFMBE Proceedings, Spinger Berlin Heidelberg, 2009, pp. 22-26.

(56) References Cited

OTHER PUBLICATIONS

Rueckert, D. et al., "Nonrigid Registration Using Free-Form Deformations: Application to Breast MR Images," IEEE Transactions on Medical Imaging, vol. 19, No. 8, Aug. 1999, pp. 712-721.
Zarins, C. K. et al., "Cartoid Bifurcation Atherosclerosis. Quantitative Correlation of Plaque Localization with Flow Velocity Profiles and Wall Shear Stress," Circulation Research, vol. 53, 1983, pp. 502-514.
Asakura, T. et al., "Flow Patterns and Spatial Distribution of Atherosclerotic Lesions in Human Coronary Arteries," Circulation Research, vol. 66, Apr. 1990, pp. 1045-1066.
Katritsis, D. G. et al., "Anatomic Characteristics of Culprit Sites in Acute Coronary Syndromes," Journal of Interventional Cardiology, vol. 21, No. 2, Apr. 2008, pp. 140-150.
Ciompi, F. et al., "Reconstruction and Analysis of Intravascular Ultrasound Sequences," New Advances in Biomedical Signal Processing, Ch. 16, Bentham Science, 2011, pp. 231-250.
Wette, P. et al., "Extending the Corkscrew Algorithm to Find Bifurcations of Vessels," Computer Graphics and Imaging, Innsbruck, Austria, 2010, 7 pages.
Zhou, J. et al., "Vascular Structure Segmentation and Bifurcation Detection," International Symposium on Biomedical Imaging, Apr. 2007, pp. 872-875.
Koehler, H. et al., "Extraction and Analysis of Coronary-Tree from Single X-Ray Angiographies," Medical Imaging, 2004, pp. 810-819.
Bhuiyan, A. et al., "Automatic Detection of Vascular Bifurcations and Crossovers from Color Retinal Fundus Images," Proceedings of the 2007 3rd International IEEE Conference on Signal-Image Technologies and Internet-Based System, Dec. 2007, pp. 662-669.
Zhang, X. et al., "Tissue Characterizatoin in Intravascular Ultrasound Images," IEEE Transaction on Medical Imaging, vol. 17, No. 6, Dec. 1998, pp. 889-899.
Pujol, O. et al., "Intravascular Ultrasound Images Vessel Characterization Using AdaBoost," In Functional Imaging and Modelling of the Heart: Lecture Notes in Computer Science, 2003, pp. 242-251.
Caballero, K. L. et al., "Using Reconstructed IVUS Images for Coronary Plaque Classification," Proceedings of the 29th Annual International Conference of the IEEE Engineering in Medicine and Biology Society, Aug. 2007, 2167-2170.
Rotger, D. et al., "Automatic Detection of Bioabsorbable Coronary Stents in IVUS Images Using a Cascade of Classifiers," IEEE Transactions on Information Technology in Biomedicine, vol. 14, No. 2, Mar. 2010, pp. 535-537.
Gatta, C. et al., "Robust Image-Based IVUS Pullbacks Gating," MICCAI '08: Proceedings of the 11th International Conference on Medical Image Computing and Computer-Assisted Intervention, Part II, Berlin, Heidelberg, Springer-Verlag, 2008, pp. 518-525.
Gatta, C. et al., Fast Rigid Registration of Vascular Structures in IVUS Sequences, IEEE Transactions on Information Technology in Biomedicine, vol. 13, Nov. 2009. pp. 1006-1011.
Frame, A. et al., "Structural analysis of Retinal Vessels," 6th International Conference on Image Processing and its Applications, 1997, vol. 2, Jul. 1997, pp. 824-827.
Bovik, A. et al., "Multichannel Texture Analysis Using Localized Spatial Filters," IEEE Transactions on Pattern Analysis and Machine Intelligence, vol. 12, No. 1, Jan. 1990, pp. 55-73.
Ojala, T. et al., "Multiresolution Gray-Scale and Rotation Invariant Texture Classification with Local Binary Patterns," IEEE Transactions on Pattern Analysis and Machine Intelligence, vol. 24, No. 7, Jul. 2002, pp. 971-987.

Kudo, N. et al., "In Vitro Study on Arterial Lumen Detection using a Correlation Technique in IVUS," Proceedings of the 20th Annual International Conference of the IEEE Engineering in Medicine and Biology Society, vol. 20, No. 2, Oct. 29, 1998, pp. 830-831.
Li, W. et al., "Temporal Correlation of Blood Scattering Signals in Vivo from Radiofrequency Intravascular Ultrasound," Ultrasound in Medicine and Biology vol. 22, No. 5, 1996, pp. 583-590.
Alberti, M. et al., "Automatic Branching Detection in IVUS Sequences," Proceedings of the 5th Iberian Conference on Pattern Recognition and Image Analysis, No. 6669, Springer-Verlag, 2011, pp. 126-133.
Breiman, L., "Random Forests," Machine Learning, vol. 45, Oct. 2001, pp. 5-32.
Bruining, N. et al., "Dynamic Three-Dimensional Reconstruction of ICUS Images Based on ECG-Gated Pull-Back Device," 18th Annual International Conference of the IEEE Engineering in Medicine and Biology Society, 1996, pp. 633-635.
Ciompi, F. et al., "Fusing in-Vitro and in Vivo intravascular Ultrasound Data for Plaque Characterization," International Journal of Cardiovascular Imaging, vol. 26, 2010, pp. 763-779.
Cohen, W. W., "Stacked Sequential Learning," International Joint Conference on Artificial Intelligence, 2005, pp. 671-676.
Colombo, A. et al., "Randomized Study to Evaluate Sirolimus-Eluting Stents Implanted at Coronary Bifurcation Lesions," Circulation, vol. 109, 2004, pp. 1244-1249.
Costa, R. A. et al., "Bifurcation Lesion Morphology and Intravascular Ultrasound Assessment," the International Journal of Cardiovascular Imaging, vol. 27, No. 2, 2011, pp. 189-196.
Davies, M. J. et al., "Plaque Fissuring—The Cause of Acute Myocardial Infarction, Sudden Ischaemic Death, and Crescendo Angina," British Heart Journal, vol. 53, 1985, pp. 363-373.
Demsar, J., "Statistical Comparisons of Classifiers over Multiple Data Sets," Journal of Machine Learning Research, vol. 7, 2006, pp. 1-30.
Dietterich, T. G., "Machine Learning for Sequential Data: A Review," Structural, Syntactic, and Statistical Pattern Recognition, Spinger-Verlag, 2002, pp. 15-30.
Freund, Y. et al., "A Decision-Theoretic Generalization of On-Line Learning and an Application to Boosting," Journal of Computer and System Sciences, vol. 55, No. 1, 1997, pp. 119-139.
Fuster, V. et al., "Atherothrombosis and High-Risk Plaque: Part I: Evolving Concepts," Journal of the American College of Cardiology, vol. 46, No. 6, 2005, pp. 937-954.
Kimura, B. J. et al., "Atheroma Morphology and Distribution in Proximal Left Anterior Descending Coronary Artery: in Vivo Observations," Journal of the American College of Cardiology, vol. 27, No. 4, Mar. 15, 1996, pp. 825-831.
Loy, G. et al., "Fast Radial Symmetry for Detecting Points of Interest," IEEE Transactions on Pattern Analysis and Machine Intelligence, vol. 25, No. 8, Aug. 2004, pp. 959-973.
Moore, J. E. et al., "Coronary Artery Bifurcation Biomechanics and Implications for Interventional Strategies," Catheterization and Cardiovascular Interventions, vol. 76, 2010, pp. 836-843.
O'Malley, S. M. et al., "Image Based Gating of Intravascular Ultrasound Pull-Back Sequences" IEEE Transaction on Information Technology in Biomedicine, vol. 12, No. 3, May 2008, pp. 299-306.
O'Malley, S. M. et al., "One-Class Acoustic Characterization Applied to Blood Detections in IVUS," Proceedings of the 10th International Conference on Medical image Computing and Computer-Assisted Interventions, vol. 1, Berlin, Heidelberg, Springer-Verlag, 2007, pp. 202-209.
Puertas, E. et al., "Multi-class Multi-scale Stacked Sequential Learning," Proceedings of the 8th International Workshop on Multiple Classifier Systems, MSC '09, Berlin, Heidelberg, Springer-Verlag, 2009, pp. 262-271.

* cited by examiner

SYSTEMS AND METHODS FOR DETECTING AND DISPLAYING BODY LUMEN BIFURCATIONS

CROSS-REFERENCE TO RELATED APPLICATIONS

This application claims the benefit under 35 U.S.C. § 119(e) of U.S. Provisional Patent Application Ser. No. 61/416,947 filed on Nov. 24, 2010, and U.S. Provisional Patent Application Ser. No. 61/510,014 filed on Jul. 20, 2011, both of which are incorporated herein by reference.

TECHNICAL FIELD

The present invention is directed to the area of imaging systems that are insertable into a patient and methods of making and using the imaging systems. The present invention is also directed to methods and imaging systems for detecting and displaying bifurcations in body lumens, such as vascular bifurcations.

BACKGROUND

Ultrasound devices insertable into patients have proven diagnostic capabilities for a variety of diseases and disorders. For example, intravascular ultrasound ("IVUS") imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

As an example, atherosclerosis is a vascular pathology affecting in particular bifurcations in a blood vessel. The choice between different clinical treatment procedures may depend on the angle and the distribution of plaque between the main vessel and the side branch. Although IVUS imaging can provide such information, the selection of a view for bifurcation visualization may be operator-subjective. Moreover, the IVUS view may not fully display the real morphological bending and tortuosity of the vessel. Finally, the IVUS inspection is typically non-trivial and it often requires highly trained personnel for extracting information to make a clinical decision about bifurcation treatment.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
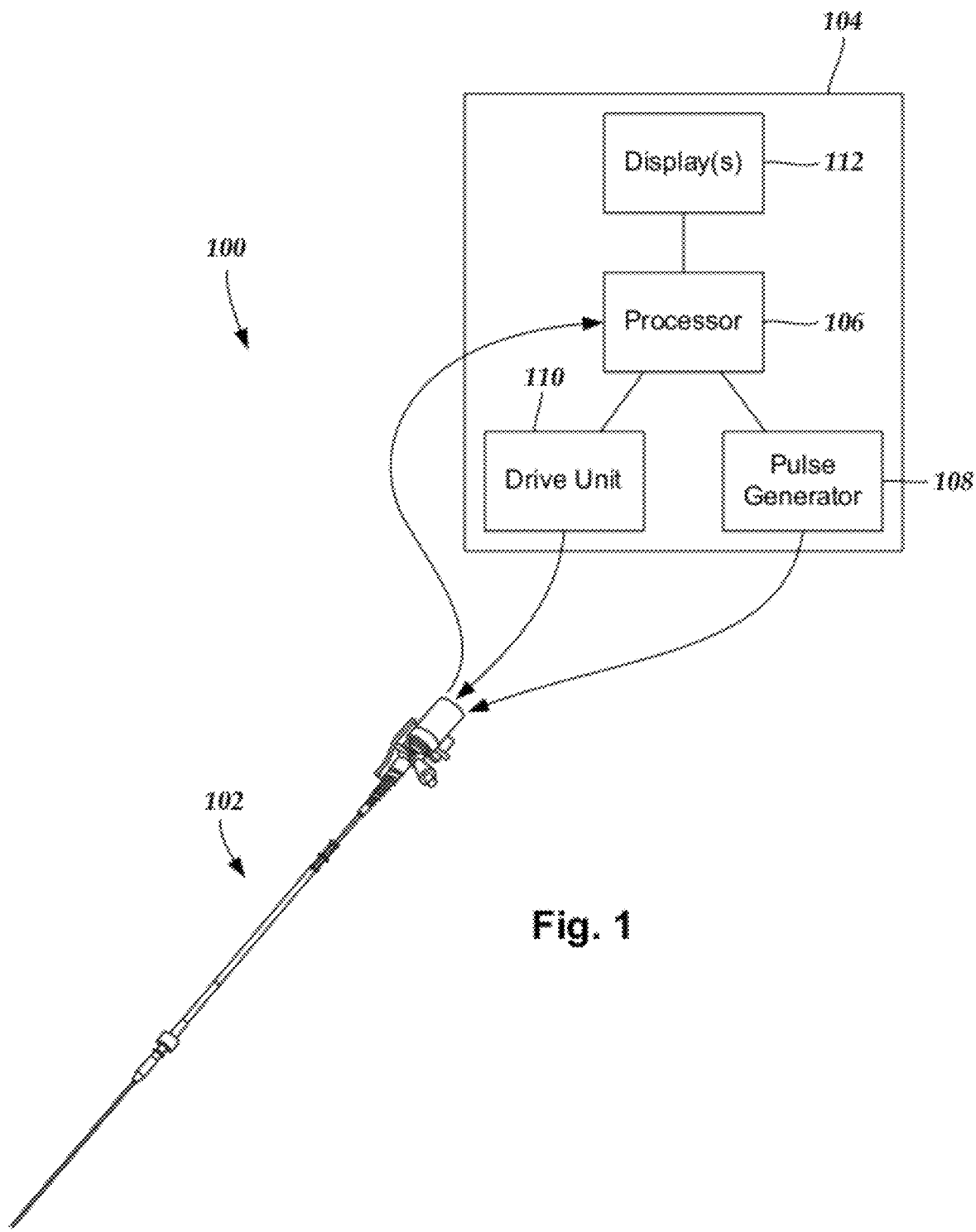
FIG. 1 is a schematic view of one embodiment of an ultrasound imaging system suitable for insertion into a patient, according to the invention.

The present invention is directed to the area of imaging systems that are insertable into a patient and methods of making and using the imaging systems. The present invention is also directed to methods and imaging systems for detecting and displaying bifurcations in body lumens, such as vascular bifurcations.

The methods, systems, and devices described herein may be embodied in many different forms and should not be construed as limited to the embodiments set forth herein. Accordingly, the methods, systems, and devices described herein may take the form of an entirely hardware embodiment, an entirely software embodiment or an embodiment combining software and hardware aspects. The methods described herein can be performed using any type of computing device, such as a computer, that includes a processor or any combination of computing devices where each device performs at least part of the process.

Suitable computing devices typically include mass memory and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

Methods of communication between devices or components of a system can include both wired and wireless (e.g., RF, optical, or infrared) communications methods and such methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Nos. 2006/0100522; 2006/0106320; 2006/0173350; 2006/0253028; 2007/0016054; and 2007/0038111; all of which are incorporated herein by reference.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric pulses that may be input to one or more transducers (312 in FIG. 3) disposed in the catheter 102.

In at least some embodiments, mechanical energy from the drive unit 110 may be used to drive an imaging core (306 in FIG. 3) disposed in the catheter 102. In at least some embodiments, electric signals transmitted from the one or more transducers (312 in FIG. 3) may be input to the processor 106 for processing. In at least some embodiments, the processed electric signals from the one or more transducers (312 in FIG. 3) can be displayed as one or more images on the one or more displays 112. For example, a scan converter can be used to map scan line samples (e.g., radial scan line samples, or the like) to a two-dimensional Cartesian grid to display the one or more images on the one or more displays 112.

In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
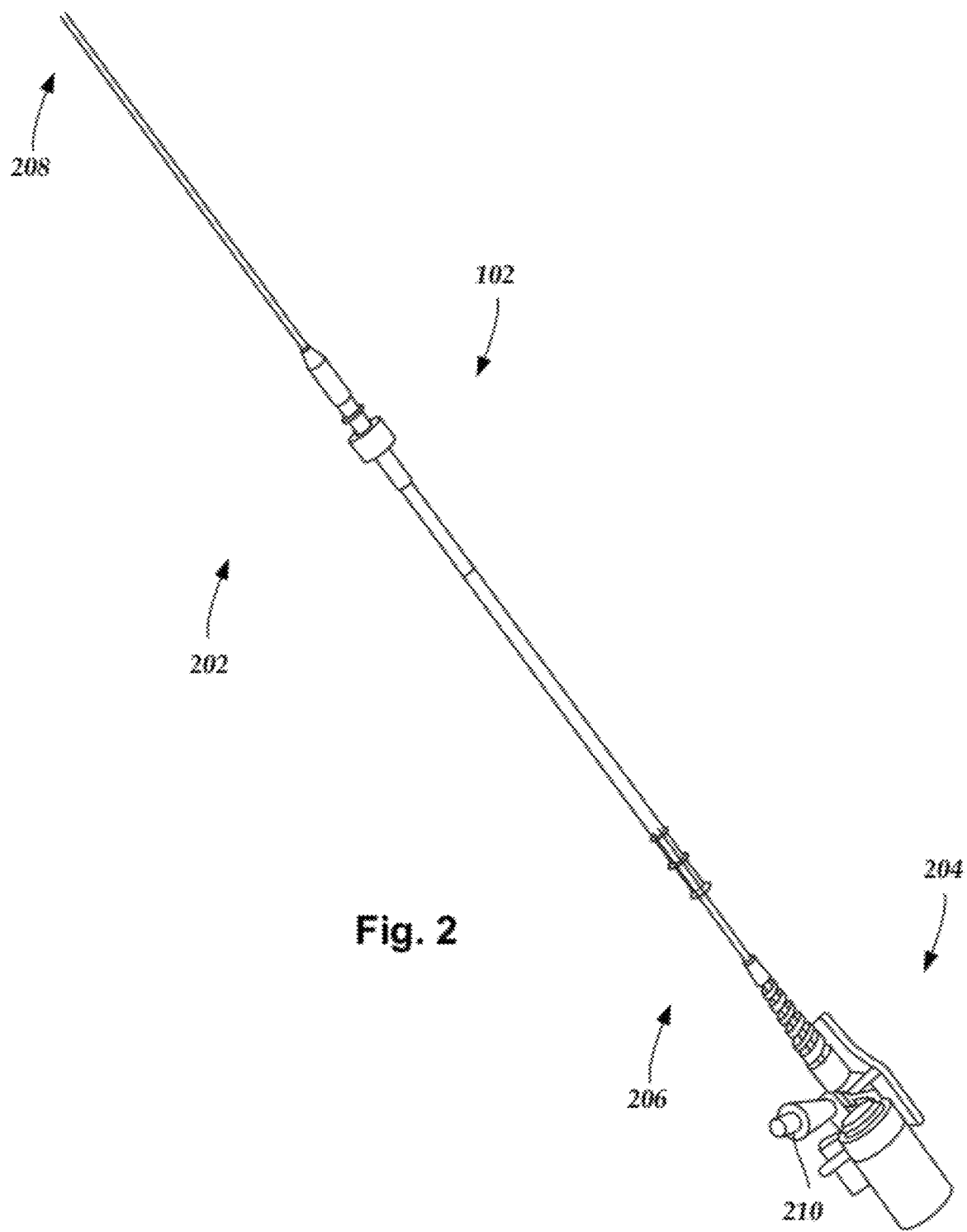
FIG. 2 is a schematic side view of one embodiment of a catheter suitable for use with the ultrasound imaging system of FIG. 1, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. Optionally, the catheter 102 may define at least one flush port, such as flush port 210. The flush port 210 may be defined in the hub 204. The hub 204 may be configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
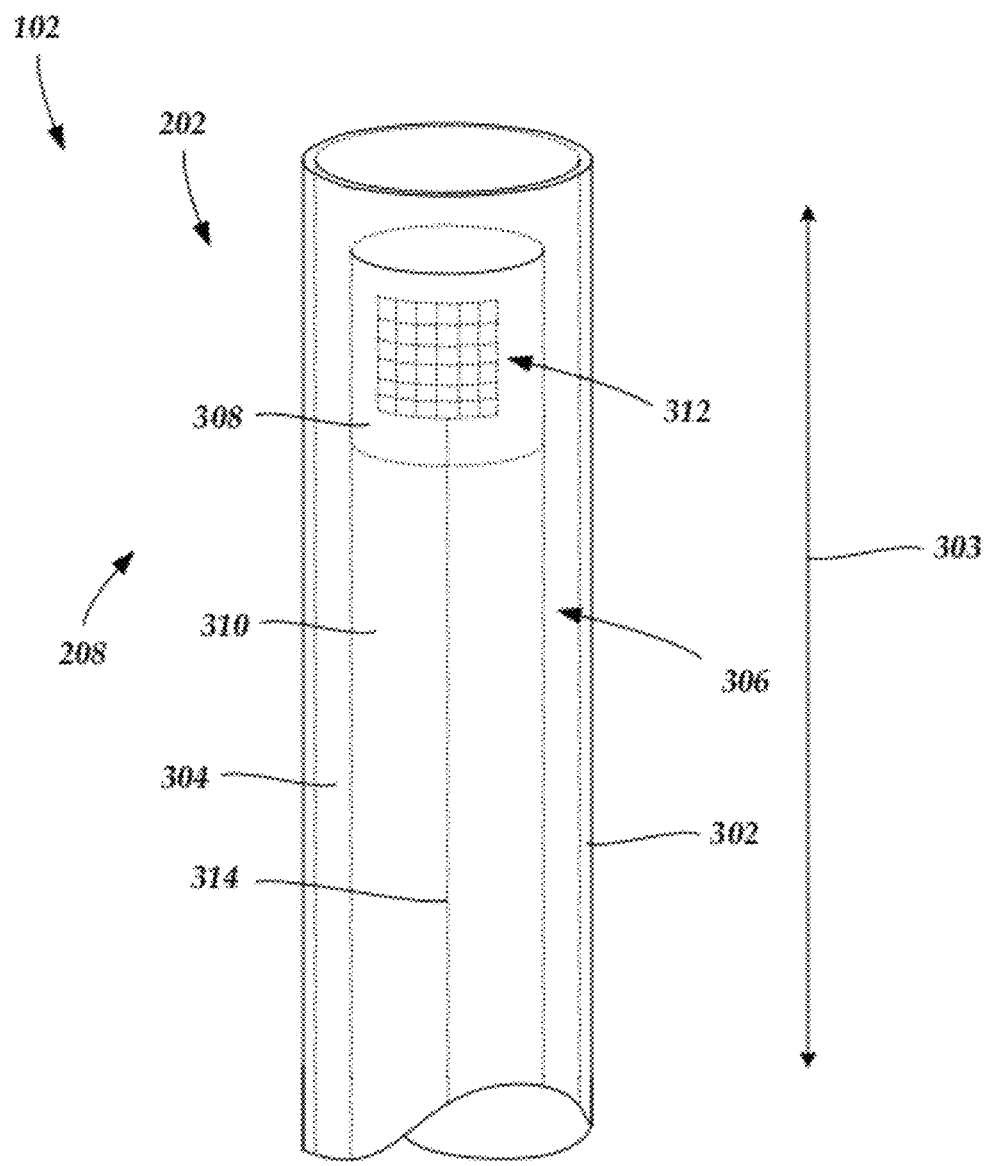
FIG. 3 is a schematic longitudinal cross-sectional view of one embodiment of a distal end of the catheter of FIG. 2 with an imaging core disposed in a lumen defined in a sheath, according to the invention.

FIG. 3 is a schematic perspective view of one embodiment of the distal end 208 of the elongated member 202 of the catheter 102. The elongated member 202 includes a sheath 302 with a longitudinal axis 303 and a lumen 304. An imaging core 306 is disposed in the lumen 304. The imaging core 306 includes an imaging device 308 coupled to a distal end of a driveshaft 310 that is rotatable either manually or using a computer-controlled drive mechanism. One or more transducers 312 may be mounted to the imaging device 308 and employed to transmit and receive acoustic signals. The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

In a preferred embodiment (as shown in FIG. 3), an array of transducers 312 are mounted to the imaging device 308. In alternate embodiments, a single transducer may be employed. Any suitable number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 312 are employed, the transducers 312 can be configured into any suitable arrangement including, for example, an annular arrangement, a rectangular arrangement, or the like.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like)

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a matching layer and a conductive backing material formed from an acoustically absorbent material (e.g., an epoxy substrate with tungsten particles). During operation, the piezoelectric layer may be electrically excited to cause the emission of acoustic pulses.

The one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

The imaging core 306 is rotated about the longitudinal axis 303 of the catheter 102. As the imaging core 306 rotates, the one or more transducers 312 emit acoustic signals in different radial directions (i.e., along different radial scan lines). For example, the one or more transducers 312 can emit acoustic signals at regular (or irregular) increments, such as 256 radial scan lines per revolution, or the like. It will be understood that other numbers of radial scan lines can be emitted per revolution, instead.

When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In at least some embodiments, the rotation of the imaging core 306 is driven by the drive unit 110 disposed in the control module (104 in FIG. 1). In alternate embodiments, the one or more transducers 312 are fixed in place and do not rotate. In which case, the driveshaft 310 may, instead, rotate a mirror that reflects acoustic signals to and from the fixed one or more transducers 312.

When the one or more transducers 312 are rotated about the longitudinal axis 303 of the catheter 102 emitting acoustic pulses, a plurality of images can be formed that collectively form a radial cross-sectional image (e.g., a tomographic image) of a portion of the region surrounding the one or more transducers 312, such as the walls of a blood vessel of interest and tissue surrounding the blood vessel. The radial cross-sectional image can, optionally, be displayed on one or more displays 112. The at least one of the imaging core 306 can be either manually rotated or rotated using a computer-controlled mechanism.

The imaging core 306 may also move longitudinally along the blood vessel within which the catheter 102 is inserted so that a plurality of cross-sectional images may be formed along a longitudinal length of the blood vessel. During an imaging procedure the one or more transducers 312 may be retracted (i.e., pulled back) along the longitudinal length of the catheter 102. The catheter 102 can include at least one telescoping section that can be retracted during pullback of the one or more transducers 312. In at least some embodiments, the drive unit 110 drives the pullback of the imaging core 306 within the catheter 102. The drive unit 110 pullback distance of the imaging core can be any suitable distance including, for example, at least 5 cm, 10 cm, 15 cm, 20 cm, 25 cm, or more. The entire catheter 102 can be retracted during an imaging procedure either with or without the imaging core 306 moving longitudinally independently of the catheter 102.

A stepper motor may, optionally, be used to pull back the imaging core 306. The stepper motor can pull back the imaging core 306 a short distance and stop long enough for the one or more transducers 306 to capture an image or series of images before pulling back the imaging core 306 another short distance and again capturing another image or series of images, and so on.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 100 MHz.

One or more conductors 314 can electrically couple the transducers 312 to the control module 104 (see e.g., FIG. 1). In which case, the one or more conductors 314 may extend along a longitudinal length of the rotatable driveshaft 310.

The catheter 102 with one or more transducers 312 mounted to the distal end 208 of the imaging core 308 may be inserted percutaneously into a patient via an accessible blood vessel, such as the femoral artery, femoral vein, or jugular vein, at a site remote from the selected portion of the selected region, such as a blood vessel, to be imaged. The catheter 102 may then be advanced through the blood vessels of the patient to the selected imaging site, such as a portion of a selected blood vessel.

An image frame ("frame") of a composite image can be generated each time one or more acoustic signals are output to surrounding tissue and one or more corresponding echo signals are received by the imager 308 and transmitted to the processor 106. A plurality (e.g., a sequence) of frames may be acquired over time during any type of movement of the imaging device 308. For example, the frames can be acquired during rotation and pullback of the imaging device 308 along the target imaging location. It will be understood that frames may be acquired both with or without rotation and with or without pullback of the imaging device 308. Moreover, it will be understood that frames may be acquired using other types of movement procedures in addition to, or in lieu of, at least one of rotation or pullback of the imaging device 308.

In at least some embodiments, when pullback is performed, the pullback may be at a constant rate, thus providing a tool for potential applications able to compute longitudinal vessel/plaque measurements. In at least some embodiments, the imaging device 308 is pulled back at a constant rate of at least 0.3 mm/s. In at least some embodiments, the imaging device 308 is pulled back at a constant rate of at least 0.4 mm/s. In at least some embodiments, the imaging device 308 is pulled back at a constant rate of at least 0.5 mm/s. In at least some embodiments, the imaging device 308 is pulled back at a constant rate of at least 0.6 mm/s. In at least some embodiments, the imaging device 308 is pulled back at a constant rate of at least 0.7 mm/s. In at least some embodiments, the imaging device 308 is pulled back at a constant rate of at least 0.8 mm/s.

In at least some embodiments, the one or more acoustic signals are output to surrounding tissue at constant intervals of time. In at least some embodiments, the one or more corresponding echo signals are received by the imager 308 and transmitted to the processor 106 at constant intervals of time. In at least some embodiments, the resulting frames are generated at constant intervals of time.

Figure 4:
FIG. 4 is a schematic diagram illustrating two IVUS views—a short-axis view and a longitudinal view.

FIG. 4 illustrates two conventional IVUS image views. The short-axis view 402 represents a single image of the sequence, and the longitudinal view (or long-axis view) 404 represents a transversal cut of the three dimensional pullback. The current longitudinal view represents the pullback as a bi-dimensional pipe centered along the catheter position and does not illustrate the real morphological bending and tortuosity of the vessel.

In contrast, the anatomical morphology of both the main vessel and its branching are assessed by angiographic imaging. For the best choice of the most appropriate vessel treatment a clinician may switch between the IVUS and the angiographic visualization in order to mentally find a correspondence between the IVUS frame and its position in the angiography projection.

The present invention is directed, at least in part, to alignment of an IVUS longitudinal image with an angiographic projection resulting in a revised non-linear IVUS longitudinal view that illustrates the bending of a vessel at a bifurcation of the vessel. The resulting revised IVUS longitudinal view could be referred to as an IVUS roadmap view and can combine the high resolution plaque analysis provided IVUS with the anatomical morphology information of an angiographic projection.

Figure 5:
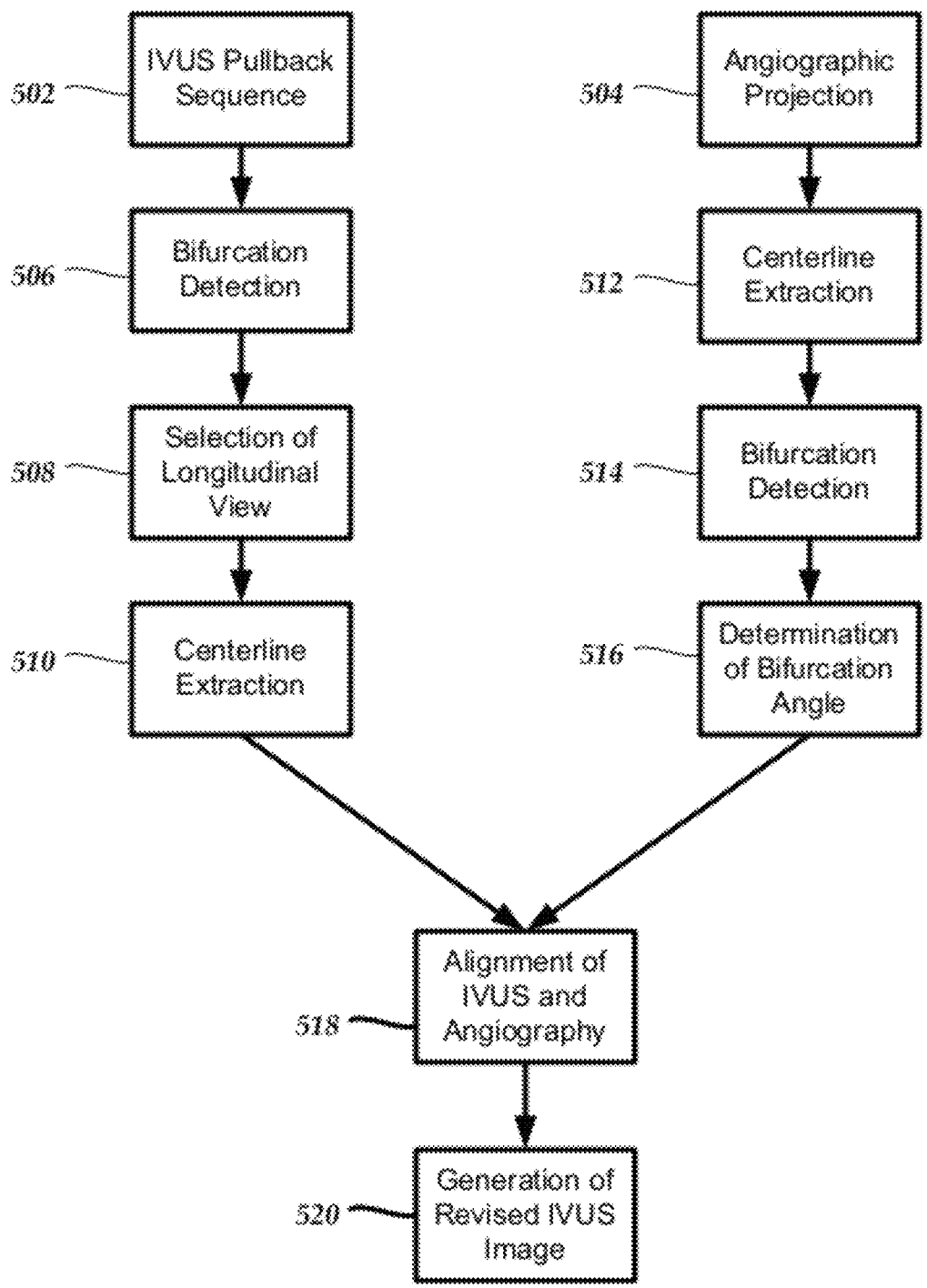
FIG. 5 is a schematic block diagram illustrating a work flow for one embodiment of a method of identifying a bifurcation in a body lumen and preparing a revised IVUS longitudinal view illustrating the bifurcation, according to the invention.

FIG. 5 illustrates one embodiment of a flow for analyzing IVUS data and displaying a revised IVUS longitudinal view that incorporates morphological information regarding bifurcations. The method includes the acquisition of two sequences of data for the same body lumen (e.g., blood vessel): an IVUS pullback sequence 502 (e.g., a sequence of IVUS frames obtained during a pullback procedure) and an angiographic projection 504. Any suitable IVUS and angiographic methods and devices can be used to obtain the IVUS pullback sequence and the angiographic projection. Such methods and devices are well-known.

The IVUS pullback sequence is analyzed to identify bifurcations in the body lumen (box 506). Any suitable method for bifurcation can be used including manual or automated detection or combinations thereof. The analysis of the IVUS frames for bifurcation detection can include, for example, using an automated classifier that is trained to identify bifurcations. In one embodiment, the classifier is defined as a binary classifier for distinguishing the angular sectors of the IVUS frames containing a bifurcation from the others. In some embodiments, this classification is achieved using a computer vision approach in which each image frame of a sequence is automatically classified using texture analysis. In at least some embodiments, the classifier is trained using a database of IVUS frames that have been manually identified.

As an example of classification, in an IVUS pullback sequence the vessel lumen eccentricity typically increases in bifurcation regions. Accordingly, a classifier can analyze one or more multi-scale textural and radial properties of the vessel in order to identify eccentricity variations. Additional examples of classifiers and classification methodologies are discussed hereinbelow.

In at least some embodiments, the IVUS pullback sequence is stabilized prior to classification to compensate for motion artifacts caused by heart beating. Any suitable motion stabilization technique can be used including the techniques described in U.S. patent application Ser. No. 12/898,437, incorporated herein by reference. Subsequently, classification is performed using a machine learning technique, in which a classifier has been trained using a database of previously analyzed IVUS frames. Preferably, these IVUS frames have been manually labeled by experts. For each pullback sequence, the results of the classification between bifurcation and non-bifurcation angular sectors can be optionally graphically represented as one or more parametric classification maps M, where, for example, the angular and longitudinal positions along the pullback sequence are represented on the horizontal and vertical axes respectively. The parametric map or maps M can be obtained using known methods for generating such maps.

The results of the classification can be refined by considering the spatio-temporal continuity of the bifurcation regions, thus exploiting the neighborhood relations of pixels in the parametric map or maps. For each bifurcation, an estimate of the centers and both longitudinal (temporal) and angular (orientation) extension of each bifurcation can be obtained.

Given a pullback sequence of IVUS images, which can be defined as I(x, y, t), where x, and y are the vertical and horizontal coordinates of an Cartesian IVUS frame, t is the longitudinal coordinate along the pullback, one or more bifurcation longitudinal views can be selected (box 508). Each bifurcation longitudinal view corresponds to a bi-dimensional cut I(ρ, t) of the sequence in which a bifurcation is visible, where ρ is the angular coordinate of the IVUS frame. The coordinate ρ is preferably obtained as the center of a bifurcation that has been identified, for example, manually, automatically, or from a parametric map M.

Figure 6A:
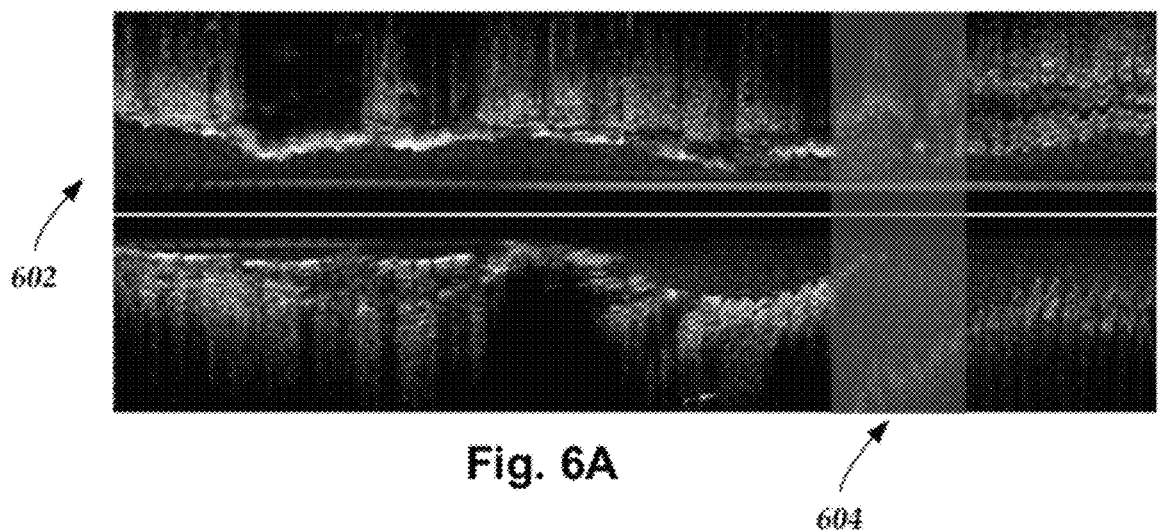
FIG. 6A is a schematic IVUS longitudinal view with identification of a bifurcation, according to the invention.
Figures 6B, 7:
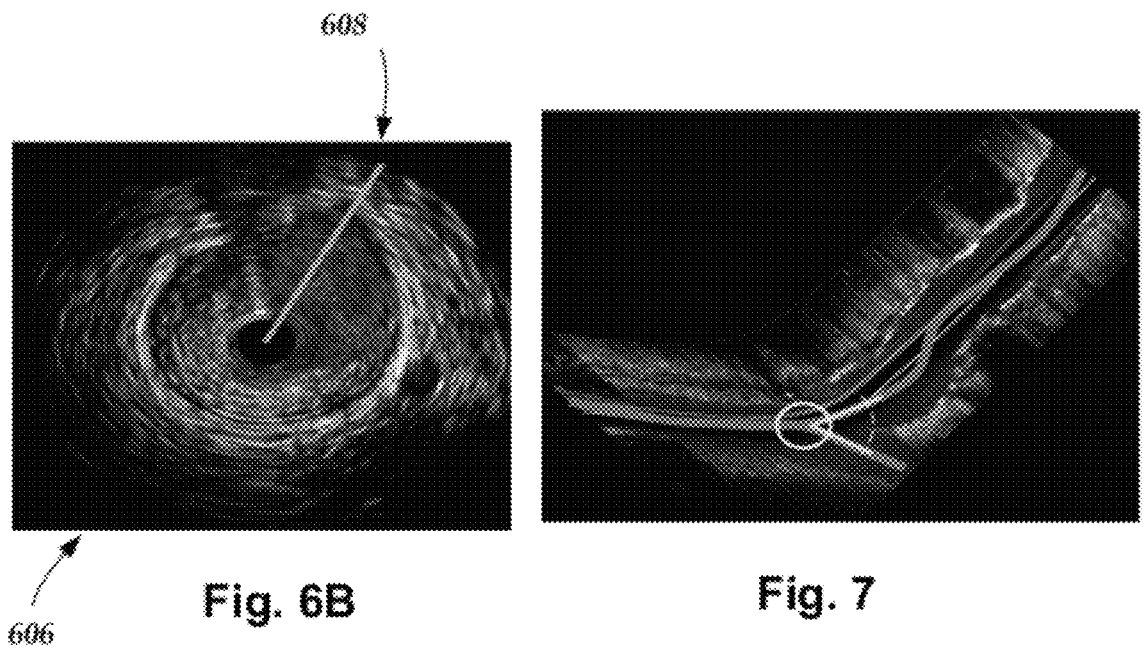
FIG. 6B is a schematic IVUS short-axis view with identification of a bifurcation, according to the invention.
FIG. 7 is a schematic revised IVUS longitudinal view with portions of the longitudinal view disposed with respect to a bifurcation angle, according to the invention.

FIG. 6A illustrates one example of a longitudinal view 602 in which the identified bifurcation area 604 is shaded on the grayscale IVUS pullback longitudinal view. In FIG. 6B a single frame 606 belonging to the bifurcation area is shown. The line 608 represents the selected angle ρ generating the longitudinal view of FIG. 6A.

The lumen area can be successively extracted from the selected bifurcation longitudinal view using an automatic segmentation method (see, e.g., Ciompi, et al., Med Image Comput Assist Interv, 12, 869-76 (2009), incorporated herein by reference) and the corresponding vessel centerline is computed from the lumen contours (box 510). Any suitable method can be used for automatic segmentation and vessel centerline computation. The combined information of the centerline and of the bifurcation location represents a landmark for the angiographic and IVUS alignment.

Turning to the angiographic projection 504, the extraction of the vessel anatomical morphology from the single-plane angiographic sequence includes the selection of a frame in which vessels of interest are visible. In at least some embodiments, the frame is independent from the X-ray imager used as the selection of the frame uses only data exported by the angiographic system. A centerline is extracted (box 512) from the single-plane angiographic projection to provide the skeleton of the main vessel and its branching (see, e.g., Magjarevic, et al., 13$^{th}$ International Conference on Biomedical Engineering, IFMBE Proceedings, pp. 22-26 (2009), incorporated herein by reference). Any suitable centerline extraction method can be used. Bifurcations are then detected (box 514) and an estimation of the bifurcation angle (box 516) is computed from the centerlines of the two branches.

The alignment of the IVUS bifurcation longitudinal view and the angiographic projection includes the extraction of the centerline and bifurcation shape in both imaging modalities, as described above. A geometric alignment (box 518) of the two imaging modalities can be obtained using any suitable technique. For example, in at least some embodiments, a geometric alignment can be obtained by computing a non-rigid transformation T between the centerlines that transforms the IVUS data to the vessel shape extracted from the angiographic projection. Optionally, the branching positions (i.e., bifurcations) can be used as landmarks to develop a robust correspondence between both shapes.

From the alignment (e.g., from the geometric transformation T) a revised IVUS image can be obtained (box 520) deforming portions of the IVUS longitudinal image using the morphology of the angiographic projection. For example, the portions of the IVUS longitudinal image can be deformed using a non-rigid registration method based on B-spline regularization. FIG. 7 illustrates one example of a revised IVUS image formed using this process. The orientation of the artery follows the anatomical morphology of the angiographic image.

The revised IVUS longitudinal image can enhance the clinical value of an IVUS imaging system. This revised view can enhance the ability to diagnose vessel bifurcation regions which can be an important location for plaque growth and rupture.

As indicated above, one part of the process of forming a revised IVUS longitudinal image is the identification of bifurcations in the IVUS data. Any suitable identification method can be used including methods of classifying structures in the IVUS data. Such classification methods have been used for tissue classification and can be adapted to identification of bifurcations. Examples of tissue classification methods that can be adapted include, but are not limited to, those methods described in U.S. Pat. Nos. 7,460,716, 7,680,307, and 7,729,533 and U.S. patent application Ser. Nos. 12/253,471, 12/429,005, and 12/563,754, all of which are incorporated herein by reference.

Figure 8:
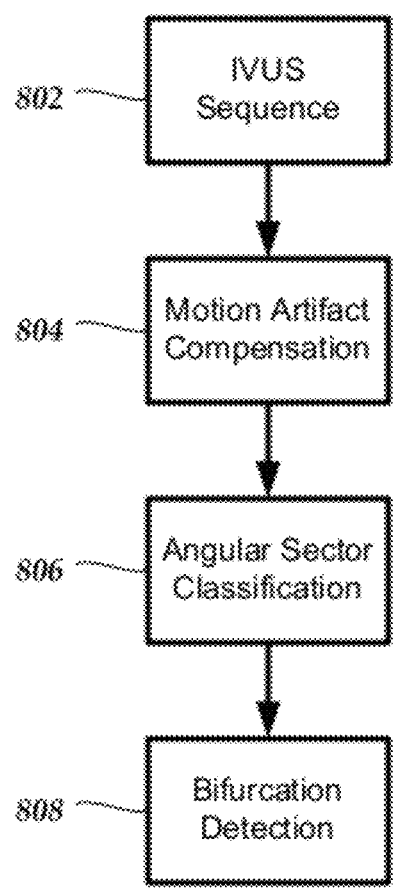
FIG. 8 is a schematic block diagram illustrating one embodiment of a method for classifying IVUS data to identify bifurcations, according to the invention.

FIG. 8 illustrates a workflow for one embodiment of a method of classification. An IVUS frame or sequence of frames is provided (box 802). The IVUS frame or sequence is optionally compensated for motion artifacts (box 804) due to, for example, the heart beating. Then, each angular sector in a pullback is classified as bifurcation or not (box 806) and bifurcations are detected (box 808). Further detail regarding this procedure is provided below.

As indicated, the IVUS data can be compensated for motion artifacts. During an IVUS pullback acquisition, the catheter can be affected by several motion artifacts. One particularly relevant motion artifact is caused by the heart beating, which may generate a repetitive longitudinal oscillation of the catheter (swinging effect) along the axis of the vessel, resulting in a possible multiple sampling of the same vessel positions. In order to obtain a unique reconstruction of the vessel transversal sections, one possible solution is the selection of the optimally stable frames, performed by image-based gating as described, for example, in U.S. patent application Ser. No. 12/898,437, incorporated herein by reference. A second undesired motion artifact is represented by catheter fluctuation causing a spatial misalignment of consecutive frames with respect to the real vessel morphology. In order to align the vessel centers in successive frames, an IVUS registration method can be employed. Any suitable registration method can be used including, but not limited to, a rigid translation of subsequent frames of a gated sequence. One example of a suitable registration methods is found in Gatta, et al., IEEE Trans Inf Technol Biomed, 13, 1006-1011 (November 2009), incorporated herein by reference.

To identify bifurcations in IVUS pullback sequences, one method of classification includes defining a binary classification problem which is aimed at distinguishing between the frames containing a bifurcation from the others. This task can be accomplished using a pattern recognition technique in which a classifier is firstly trained by using a database of IVUS frames that are manually labeled and then the classifier is applied to frames of the IVUS pullback sequence. In one embodiment, the AdaBoost algorithm with Decision Stump weak classifier is chosen for its computational simplicity and speed. It will be recognized that other pattern recognition methods can be used including other classifiers and algorithms.

As an example, in an IVUS pullback sequence the vessel lumen eccentricity typically increases in correspondence of a bifurcation. Consequently, the radial properties of the vessel texture can be analyzed to identify eccentricity variations. In at least some embodiments, the IVUS pullback can be converted to polar coordinates, where an angular sector corresponds to a column:

$$I(x,y) \in \mathbb{R} \to I(\rho,r) \in \mathbb{R}^{N_m}$$

where I is the IVUS image, x and y are the horizontal and vertical coordinates in the Cartesian system, and r and $\rho$ are the radial and angular coordinates in the polar system.

Following a texture analysis approach a set of one or more ($N_m$) parametric maps M can be extracted:

$$I(\rho,r) \in \mathbb{R} \to M(\rho,r) \in \mathbb{R}^{N_m}$$

Any suitable method can be used to prepare the parametric maps. For example, such maps can be computed by applying Gabor filters (see, e.g., Bovik, et al., IEEE Transactions on Pattern Analysis and Machine Intelligence, 12, 55-73 (1990), incorporated herein by reference), local binary patterns (LBP) (see, e.g., Ojala, et al., IEEE Transactions of Pattern Analysis and Machine Intelligence, 24,971-987 (2002), incorporated herein by reference) and cross-correlation transformations (see, e.g., Kudo, et al., Proc. of the 20$^{th}$ Annual International Conf. of the IEEE, 2, 830-831 (1998) and Li, et al., Ultrasound in Medicine and Biology, 22, 583-590 (1996), both of which are incorporated herein by reference) to the polar view. The gray-level image can be considered as one of the maps, as well.

For one or more (preferably, each) column of the parametric maps, a set of basic statistical features (for example, the position of the maximum, the standard deviation, the median, and the maximum values) can be computed:

$$M(\rho,r) \in \mathbb{R}^{N_m} \to f(\rho) \in \mathbb{R}^{N_F}$$

where $N_F$ is the total number of extracted features. Finally, each column $\rho$ can be described by a feature vector, obtained by concatenating all the features, $f_i=f_1, \ldots, f_{N_F}$. The feature vector or parametric maps or combinations thereof can be used to classify the portions of the IVUS data and detect bifurcations.

This method was tested on 10 IVUS sequences from coronary arteries, each sequence containing an average of 3000 frames. The classifier performance was assessed by a Leave-One-Patient-Out (LOPO) cross-validation technique over the $N_p=10$ sequences. At each validation fold, manual and automatic bifurcation detection were compared and performance is evaluated in terms of Accuracy (A), Sensitivity (S), Specificity (K), Precision (P), Normalized Precision (NP), False Alarm Ratio (FAR). The automatic bifurcation detection appeared superior with respect to at least sensitivity and lower false alarm ratio. The remaining scores are comparable for both manual and automatic bifurcation detection.

Figure 9:
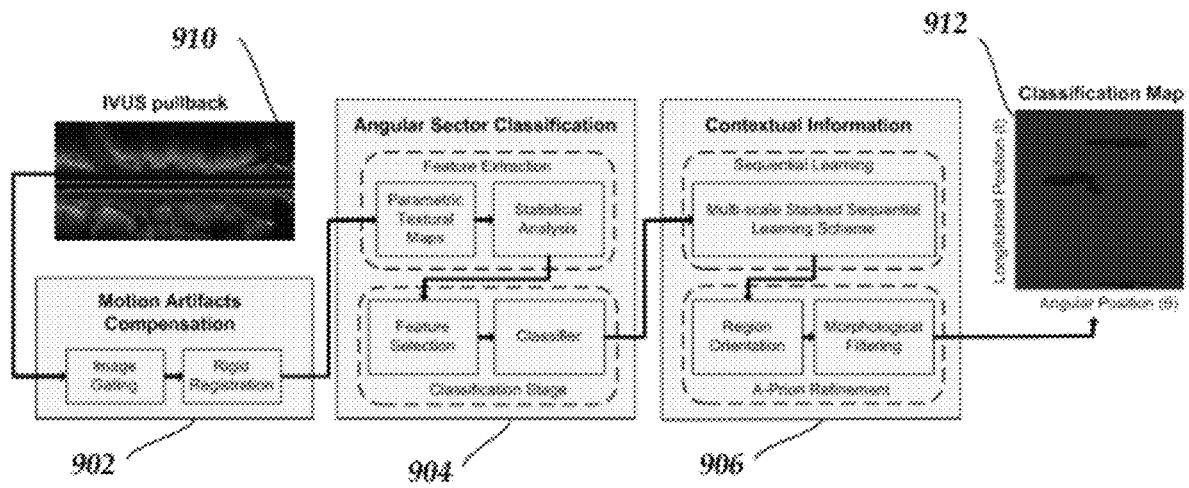
FIG. 9 is a schematic block diagram of another embodiment of a method for classifying IVUS data to identify bifurcations, according to the invention.

FIG. 9 illustrates another workflow of a method of classification. The method is divided into three consecutive stages. In the first stage 902, the IVUS sequence 910 is compensated for artifacts due to motion. In the second stage 904, each angular sector in the sequence is classified as bifurcation or not, leading to a new visualization of an IVUS pullback sequence, by organizing the sequence in a bidimensional representation in the space (θ; t), where θ is the angular position in the short-axis view and t is the longitudinal (temporal) position along the pullback. Finally, in the third stage 906 the spatial neighborhood relation among samples is exploited, both in the angular and temporal dimensions, using a stacked sequential learning (SSL) scheme and the classification results are successively refined using a-priori information about bifurcation geometries and dimensions. A classification map 912 can be generated through the process.

As indicated above, during the acquisition of an IVUS sequence, the catheter can be affected by several artifacts due to motion, interfering with the visualization, the interpretation and the analysis of the acquired sequence. One relevant artifact is caused by the heart beating, which generates a repetitive oscillation of the catheter (swinging effect) along the axis of the vessel, resulting in possible multiple sampling of the same vessel positions. In order to obtain a unique reconstruction for the transversal sections of the artery, one possible solution is the selection of the optimally stable frames, in such a way that in subsequent frames the vessel has a similar position and rotation. Such a task can be addressed by using a gating algorithm, either by exploiting the ECG signal (when it is available) or by image-based gating. For example, an image-based gating method can be used to identify the frames with minimal motion blur that can be considered as belonging to the same phase of the cardiac cycle.

Figure 10:
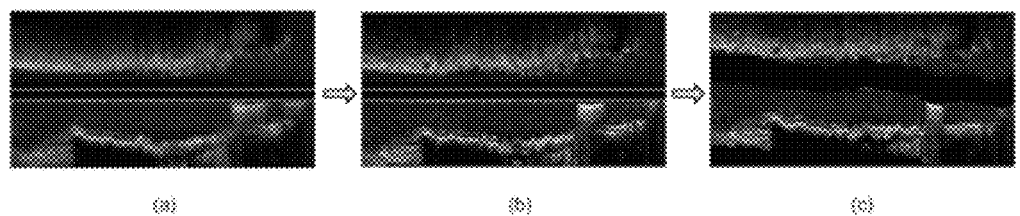
FIG. 10 includes several IVUS longitudinal views illustrating motion artifact compensation, according to the invention.

A second undesired artifact is represented by the variations in the relative positioning of the catheter with the center of the vessel, causing a spatial misalignment of consecutive frames with respect to the real vessel morphology. In this case, the arterial axis undergoes in-plane translations. In order to align the vessel centers in successive frames, an IVUS registration method can be applied using a rigid translation of subsequent frames of the gated sequence. The optimal alignment of the arterial axis is calculated by using both the position of the vessel center and the arterial radius, which are estimated by using, for example, an IVUS-tailored version of the Fast Radial Symmetry transform (see, for example, Loy et al., 7th European Conference on Computer Vision, p. 358, Springer (2002), incorporated herein by reference). FIG. 10 illustrates the results of the two successive stages of the applied artifact compensation where longitudinal view (a) corresponds to the original sequence before motion artifact compensation, longitudinal view (b) is after the application of gating, and (c) is after additional registration compensation.

In addressing the bifurcation identification task, an intuitive analysis of an IVUS frame, inspired by the visual inspection performed by physicians, includes the study of the radial textural changes of each frame. Features computed along each angular sector of the image can be extracted and analyzed. The choice of samples corresponding to angular sectors allows the definition of the angular position and the angular extension of bifurcations, which are used by physicians in the clinical practice to characterize the branchings.

Figure 11:
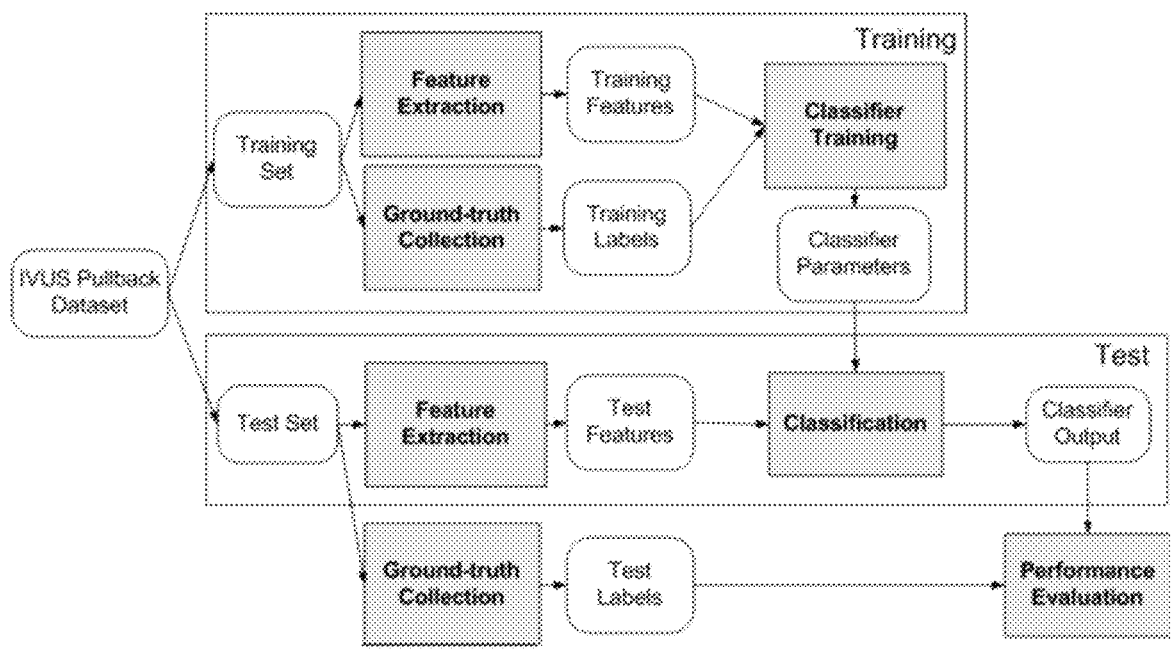
FIG. 11 is a schematic block diagram of one embodiment of a method for training and using a classifier, according to the invention.

This embodiment utilizes a pattern recognition technique, in which a binary classifier is firstly trained on a dataset of IVUS sequences, previously labeled by physicians (training phase). The classifier can then be used to identify the presence of bifurcations in new sequences (test phase). Such an arrangement is illustrated in the block diagram of FIG. 11.

In one example of a method for developing the classifier, a dataset of IVUS sequences is divided into two subsets of which one is used for the training (training set) and the other for the test (test set). For both the sets, the ground-truth collection, consisting in the creation of a reliable database of labeled ground-truth samples (separating bifurcation and non-bifurcation samples), is performed. Additionally, numeric information describing each angular sector is computed by feature extraction. This information is used for discriminating between the two classes. During the training phase, a learning algorithm learns the characteristics of the training data by analyzing the extracted training features and the corresponding labels and it produces an inferred function (defined as a classifier) as an output, with a set of parameters learned in the process. As a result, the classifier can analyze new sequences and generate their label maps. The performance of the classification can be evaluated by comparing the classification results with the corresponding test labels.

With respect to feature extraction, in most of the frames, the lumen has a pseudo-elliptical shape in the short-axis view, which typically, in the presence of bifurcations, shows higher eccentricity than in non-bifurcation frames. The radial extension of the blood region usually increases in correspondence to bifurcation angular sectors. This property can be exploited by extracting characteristics of the image texture computed along each radius of the IVUS frame. Since the applied rigid registration technique has aligned the vessel centers, homogeneous radial features can be extracted. For this purpose, the region occupied by the circular "ring down" artifact due to the catheter with a simulated blood region can be replaced. Each of the normalized images $I(x, y) \in [0, 1]$ which constitutes the sequence $S(x, y, t) \in [0, 1]$ is first converted into polar coordinates:

$$\tilde{I}(\rho,\theta)=I(\rho \cdot \cos \theta, \rho \cdot \sin \theta)$$

where x and y are the horizontal and vertical coordinates in the Cartesian system, $\rho$ and $\theta$ are the radial and angular coordinates in the polar system and t is the longitudinal (temporal) coordinate along the pullback.

A set of $N_T$ texture descriptors is defined (see, for example, Zhang, et al. IEEE Transaction on Medical Imaging, 17(6):889-899 (1998); Pujol, et al., Functional Imaging and Modeling of the Heart: Lecture Notes in Computer Science, pp. 242-251 (2003); Caballero, et al., Proceedings of the 29$^{th}$ Annual International Conference of the IEEE, EMBS, 2167-2170 (2007); Rotger, et al., IEEE Transactions on Information Technology in Biomedicine, 14(2):535-537 (2010); Ciompi, et al., International Journal of Cardiovascular Imaging, 26:763-779 (2010); and O'Malley, et al., Proceedings of the 10$^{th}$ International Conference on Medical Image Computing and Computer-Assisted Intervention— Part I, pages 202-209, Springer-Verlag (2009), each of which is incorporated herein by reference). Each descriptor specifies a mapping function:

$$F: \tilde{I}(\rho, \theta) \mapsto M_j(\rho, \theta)$$

$$M_j(\rho, \theta) \in \mathbb{R}$$

where $M_j(\rho, \theta)$ is the parametric feature map according to the $j^{th}$ textural descriptor, $j=1, 2, \ldots, N_T$. Successively, in order to extract information on the extension and eccentricity of the blood region, the statistics related to each column $\theta$ of the obtained parametric maps are considered. For each angular sector (column), basic statistical features such as, for example, one or more of (i) standard deviation, (ii) mean, (iii) median, (iv) maximum value, (v) radial position of the maximum value and (vi) histogram, are computed. To this aim, a second mapping function D is applied:

$$D: M_j(\rho, \theta) \mapsto f_i(\rho, \theta)$$

$$f_i(\rho, \theta) \in \mathbb{R}$$

where $i=1, 2, \ldots, N_S$ and $N_S$ is the total number of statistical descriptors.

Figure 12:
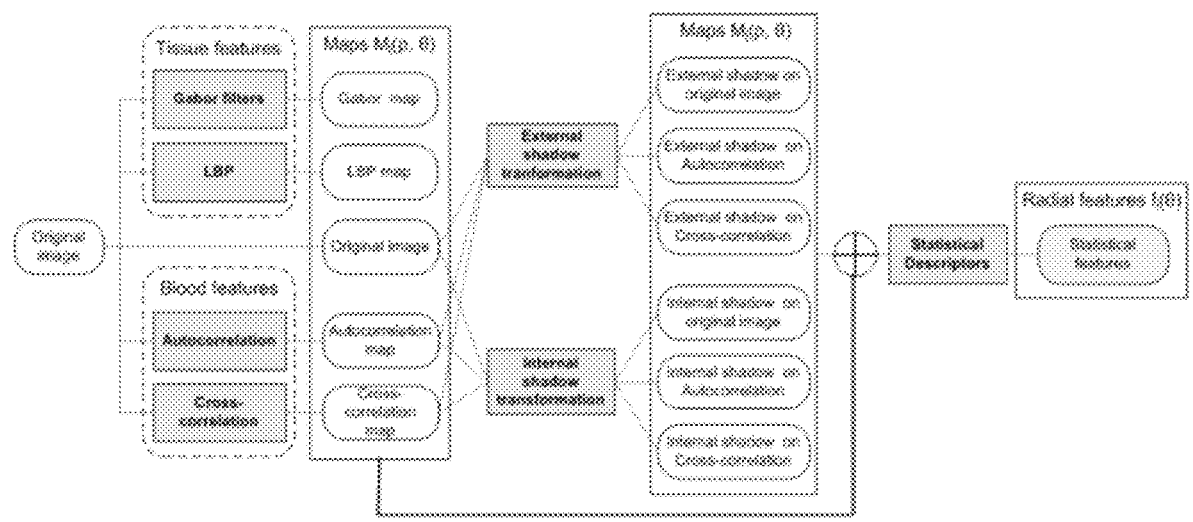
FIG. 12 is a schematic block diagram of one embodiment of a method for feature extraction, according to the invention.

In order to select the most discriminative features for the considered problem, a large set of features can be introduced and then the classifier can choose the most relevant and useful ones. The block diagram in FIG. 12 illustrates one example of the stages of a feature extraction process. Two families of textural descriptors are used in this embodiment. The first family has demonstrated its capability to characterize the tissue in IVUS images, while the second has been used to characterize the blood region.

The first feature group is composed of:
Gabor filters (see, for example, Bovik et al., IEEE Transactions on Pattern Analysis and Machine Intelligence, 12:55-73 (1990), incorporated herein by reference), a special case of wavelets of Gaussian functions modulated by a complex sinusoid. Gabor filters can extract the textural properties of the image according to a particular filter orientation.
Local Binary Patterns (LBP) (see, for example, Ojala, et al., IEEE Transactions on Pattern Analysis and Machine Intellegience, 24(7):971-987 (2002), incorporated herein by reference), applied in four configurations. LBP are used to detect uniform texture patterns in circular neighborhoods, with any quantization of angular space and spatial resolution and they are robust to brightness variations.

The second feature group is composed of:
Autocorrelation and Cross-correlation, introduced to identify repeating patterns within the same IVUS frame and among consecutive frames respectively. Both measures are calculated by using sliding windows of 3 different sizes and Cross-correlation is computed between a given frame and the successive frame in the non-gated sequence. Autocorrelation and Cross-correlation can provide useful information, since in IVUS data the blood region is expected to be less correlated than the tissue due to the rapid movement of the blood fluid, which causes scatter. On the contrary, the intensity of the vessel border is expected to remain unchanged.

The gray-level image is considered as one of the feature maps, as well. Some of the statistical descriptors computed from the gray-level image are successively normalized with respect to their average value on the whole frame.

On the original gray-level image and on the second family of parametric maps, i.e., on the Autocorrelation and Crosscorrelation maps, two additional transformations are applied, leading to the computation of the feature maps $S_{ek}(\rho, \theta)$ and $S_{ik}(\rho, \theta)$ corresponding to the input feature map $M_k(\rho, \theta)$:

$$S_{ek}(\rho, \theta) = \rho \frac{\sum_{m=\rho}^{\rho_{MAX}} M_k(\rho, \theta)}{\rho_{MAX} - \rho}$$

$$S_{ik}(\rho, \theta) = \rho \frac{\sum_{m=1}^{\rho} M_k(\rho, \theta)}{\rho}$$

where $\rho_{MAX}$ is the maximum value of the radius. The map $S_{ek}$ can be related to the presence of a shadow or to a quantification of the blood presence externally with respect to a given radial depth $\rho$, while the map $S_{ik}$ gives information about the amount of blood accumulated internally with respect to the radial position p.

In one embodiment, a total number of $N_T=26$ parametric maps, $M_j(\rho, \theta)$, is obtained. The computation of statistical features on all the parametric maps ultimately provides information about the presence of a bifurcation. For instance, the position of the maximum value in the gray-level image usually corresponds to the distance between the vessel center and the vessel border and it increases with the vessel eccentricity, while the standard deviation and the mean value along the radius typically decrease. Each angular sector $\theta$ is therefore described by a feature vector $f_i(\theta) = [f_1(\theta), f_2(\theta), \ldots, f_{N_F}(\theta)]$, where $N_F$ is the total number of considered features.

For classification, a supervised learning approach is chosen due to its higher robustness and precision, given the availability of ground-truth data and the consequent possibility of learning from examples. A discriminative classification method is applied in order to avoid the need to formulate hypothesis on the feature space. Among the existing discriminative classification methods, some may be more suited than others for the specific task of bifurcation detection. Three examples of state-of-the-art discriminative classifiers are AdaBoost, Random Forest, and Support Vector Machine.

Beyond the classifier labeling, an additional output that may be provided by the above mentioned classifiers is a classification margin $m \in [-\infty, +\infty]$, representing, in the feature space, the distance of a sample from the decision boundary. Such margin value can be interpreted as a pseudo-probability of the labeling and it can be converted into an estimate of the likelihood that a sample belongs to the bifurcation class, $p_b \in [0, 1]$.

The AdaBoost algorithm (see, for example, Freund, et al., Journal of Computer and System Sciences, 55(1):119-139

(1997), incorporated herein by reference) creates a strong classifier as a linear combination of simple weak classifiers (base learners). An iterative method allows one to keep adding base learners, until either the training error becomes lower than a given value or the number of iterations reaches a selected maximum number. An interesting quality of AdaBoost, when the base learner is a Decision Stump, is its ability to assign a weight to the features during the training stage, which can be related to the feature relevance and can be used to perform feature selection, i.e., to select a subset of relevant features for building a robust model. In fact, the Decision Stump selects, at each iteration, the single feature which best reduces the labeling error. By applying AdaBoost in this study, one can take advantage of its computational simplicity and speed.

As an example of one embodiment, at each training iteration, the AdaBoost algorithm with Decision Stump assigns a weight to each weak classifier (feature). Such weights can be used to evaluate the feature relevance. With $N_P$ the number of sequences, $N_F$ the number of initial features, i=1, 2, . . . , $N_F$ the index of each feature and $\alpha_p^i$ the weight assigned to the $i^{th}$ feature at the $p_{th}$ LOPO (Leave-One-Patient-Out) validation fold, corresponding to the $p_{th}$ pullback. The normalized weight assigned by Ada-Boost to each feature $w_f$ can be expressed as:

$$w_f = \frac{1}{N_P} \sum_{p=1}^{N_P} \frac{\alpha_p^i}{\max\{\alpha_p^1, \ldots, \alpha_p^{N_F}\}}$$

The initial set of $N_F$ features $F=\{f_1, f_2, \ldots, f_{N_F}\}$ is ordered from the most to the least relevant descriptor, creating a sorted set $F_{SORT}=\{f'_1, f'_2, \ldots, f'_{N_FS}\}$ with corresponding normalized weights $W_{SORT}=\{w_1, w_2, \ldots, w_{N_F}\}$. Subsequently, the feature subset $\tilde{F}_{SORT} \subseteq F_{SORT}$, $\tilde{F}_{SORT}=\{f'_1, f'_2, \ldots, f'_{N_S}\}$ with corresponding normalized weights $\tilde{W}_{SORT}=\{w'_1, w'_2, \ldots, w'_{N_S}\}$ is selected, comprising the most relevant $N_S$ features in $\tilde{F}_{SORT}$ whose partial cumulative weight $$cw_p = \sum_{j=1}^{N_S} w'_j$$

sums up to a percentage of the total cumulative weight set to 95%:

$$N_S : \sum_{j=1}^{N_S} w'_j = 0.95 \cdot \sum_{j=1}^{N_F} w_j S.$$

In one embodiment, the most relevant descriptors included the radial position of the maximum value, both in the gray-level image and in its parametric representations, features computed from the Gabor parametric maps, features computed from the gray-level image and features from the Cross-correlation maps.

Random Forest (see, for example, Breiman, Mach. Learn., 45:5-32, (2001), incorporated herein by reference) grows an ensemble of classification trees, where each tree votes for a class. The class produced as the output by the forest is the mode of the outputs of all the individual trees. Random Forest can robustly handle a very large number of input features. Like AdaBoost, Random Forest can measure the relevance of the features, based on the idea that randomly changing a relevant feature among those selected for building the tree affects the classification, while changing an irrelevant feature does not affect it.

The Support Vector Machine (SVM) classifier (see, for example, Cortes, et al., Mach. Learn., 20:273-297 (1995), incorporated herein by reference) performs binary classification by constructing a N-dimensional hyperplane which optimally separates the samples into two categories. In the simplest case, the hyperplane is a line. Otherwise, when the data to be discriminated are separated by a nonlinear region, instead of fitting nonlinear curves to the data SVM uses a kernel function to map the data into a different space, where a linear hyperplane can be used to separate them. Although SVM is considered an efficient classifier, the training in case of high-dimensional feature space usually suffers from high memory usage and computational complexity. Additionally, the accuracy of a SVM model largely depends on the selection of the kernel parameters, which have to be tuned implying a high computational cost during training. In general, AdaBoost and Random Forest are faster than SVM.

Figure 13:
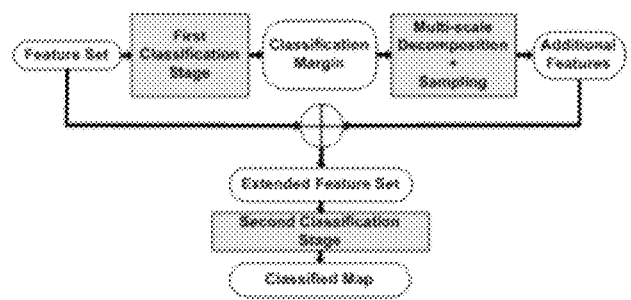
FIG. 13 is a schematic block diagram of one embodiment of a stacked sequential learning, according to the invention.

In the learning system described so far, the classification is based on the assumption that each angular sector of the IVUS images is independent of the others. However, the continuity of the branchings in pullback sequences can be additionally taken into account to enhance the classifier capabilities. There is a significant relation among neighboring angular sector samples concerning bifurcation presence, both in the longitudinal and in the angular dimensions of the sequence. The contextual information provided by neighboring samples can be exploited. The use of contextual information is potentially able to increase the performance of a machine learning system, both in terms of accuracy and precision. For example, a multi-scale Stacked Sequential Learning (SSL) scheme (see, for example, Pujol, et al., Proceedings of the 8$^{th}$ International Workshop on Multiple Classifier Systems, pages 262-271, Springer-Verlag (2009), incorporated herein by reference) can be used as a way of capturing and exploiting sequential correlations extended over multiple spatial scales. The SSL approach has been demonstrated to perform better than other state-of-the-art sequential methods. As depicted by the block diagram in FIG. 13, the multi-scale SSL scheme makes use of the feature set used in the previous classification and of the classification margin provided as an output by the classifier.

For each pullback, the classification margin values can be represented as a bidimensional pseudo-probability map in the space ($\theta$, t), illustrating the estimated likelihood of bifurcation presence, $p_b$ ($\theta$, t)$\in$[0, 1], where $\theta$ is the angular polar coordinate and t is the longitudinal (temporal) position. In the multi-scale SSL scheme, such pseudo-probability map is represented according to a multi-scale (multi-resolution) decomposition, which is sampled to obtain a set of features. This set of additional features joins the original training data features with predicted labels produced by the base classifier considering a neighborhood window. As an example, in on embodiment, a multi-scale decomposition is applied using 5 scales which leads to 45 additional features by using a 9 element neighborhood.

An extended feature set is created, consisting of the original feature set and the additional features from the SSL sampling. Finally, classification is performed on the extended feature set. The multi-resolution decomposition provides information on the spatial homogeneity and regularity of the identified bifurcation regions at different scales.

After the classification stage, the results can be refined by taking advantage of a-priori knowledge about the geometry of the coronary branchings and the characteristic dimensions of the main and side-branch vessels. Different artifacts, such as the guidewire shadow, might be confused with bifurcation regions. Indeed, when looking at a single frame (short-axis view) the appearance of a bifurcation and that of the guidewire shadow may be similar. However, since the textural pattern of the shadow is repeated along several frames of the sequence, it is possible to discriminate between the two structures by discarding, from the classification maps, the regions in which the longitudinal dimension is much more extended than the angular dimension. The orientation of the detected regions can be evaluated with respect to the longitudinal and angular axes of the classification maps to remove the regions forming an angle with respect to the θ-axis which is superior to a given threshold τ. Subsequently, in order to make the results more homogeneous and exclude regions which are too small to be bifurcations, a morphological filtering can be performed with a rectangular structuring element of size $[n_D \ n_F]$, where $n_D$ is the number of angular degrees and $n_F$ is the number of frames. In order to tune the model parameters τ, $n_F$ and $n_D$, a cross-validation process can be applied by exhaustive search.

It will be understood that each block of the block diagram illustrations, and combinations of blocks in the block diagram illustrations, as well any portion of the systems and methods disclosed herein, can be implemented by computer program instructions. These program instructions may be provided to a processor to produce a machine, such that the instructions, which execute on the processor, create means for implementing the actions specified in the block diagram block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for generating an ultrasound image, the method comprising:
   receiving a sequence of intravascular ultrasound (IVUS) data obtained as an IVUS imager moves through a body lumen;
   identifying at least one bifurcation of the body lumen from the sequence of IVUS data;
   estimating a bifurcation angle between two branches, extending from a main vessel, of the body lumen, wherein estimating the bifurcation angle comprises obtaining an angiographic projection of the body lumen; and determining the bifurcation angle from the angiographic projection; applying a geometric transformation to the IVUS data to transform at least portion of the IVUS data representing each of the two branches of the body lumen to produce a geometric alignment of the two branches according to the bifurcation angle; and
   displaying the transformed IVUS data as a non-linear IVUS longitudinal view of the body lumen with the two branches displayed in the non-linear IVUS longitudinal view according to an anatomical morphology of the two branches and the main vessel.

2. The method of claim 1, further comprising
   determining a centerline for the IVUS data through the at least one bifurcation;
   determining a centerline for the angiographic projection through the at least one bifurcation; and
   aligning the centerline for the IVUS data with the centerline for the angiographic projection.

3. The method of claim 1, wherein the sequence IVUS data comprises a plurality of frames of IVUS data and wherein identifying at least one bifurcation comprises applying at least one of the frames of IVUS data to a classifier trained to identify whether a frame contains a bifurcation of a body lumen.

4. The method of claim 1, wherein the sequence IVUS data comprises a plurality of frames of IVUS data and wherein identifying at least one bifurcation comprises observing an eccentricity of a lumen of in one or more frames of the IVUS data.

5. A non-transitory computer-readable medium having processor-executable instructions for generating an ultrasound image, the processor-executable instructions when installed onto a device enable the device to perform actions, comprising:
   receiving a sequence of intravascular ultrasound (IVUS) data obtained as an IVUS imager moves through a body lumen;
   identifying at least one bifurcation of the body lumen from the sequence of IVUS data;
   estimating a bifurcation angle between two branches, extending from a main vessel, of the body lumen, wherein estimating the bifurcation angle comprises obtaining an angiographic projection of the body lumen; and determining the bifurcation angle from the angiographic projection; and applying a geometric transformation to the IVUS data to transform at least portion of the IVUS data representing each of the two branches of the body lumen to produce a geometric alignment of the two branches according to the bifurcation angle; and
   displaying the transformed IVUS data as a non-linear IVUS longitudinal view of the body lumen with the two branches displayed in the non-linear IVUS longitudinal view according to an anatomical morphology of the two branches and the main vessel.

6. The non-transitory computer-readable medium of claim 5, wherein the processor-executable instructions further comprise
determining a centerline for the IVUS data through the at least one bifurcation;
determining a centerline for the angiographic projection through the at least one bifurcation; and
aligning the centerline for the IVUS data with the centerline for the angiographic projection.

7. The non-transitory computer-readable medium of claim 5, wherein the sequence IVUS data comprises a plurality of frames of IVUS data and wherein identifying at least one bifurcation comprises applying at least one of the frames of IVUS data to a classifier trained to identify whether a frame contains a bifurcation of a body lumen.

8. The non-transitory computer-readable medium of claim 5, wherein the sequence IVUS data comprises a plurality of frames of IVUS data and wherein identifying at least one bifurcation comprises observing an eccentricity of a lumen of in one or more frames of the IVUS data.

9. A system for generating ultrasound images, comprising:
a catheter;
an ultrasound imaging core insertable into the catheter, the ultrasound imaging core comprising at least one transducer and configured and arranged for rotation of at least a portion of the ultrasound imaging core to provide a plurality of radial scan lines;
a processor, coupleable to the ultrasound imaging core, for executing processor-readable instructions that enable actions, including:
receiving a sequence of intravascular ultrasound (IVUS) data from the ultrasound imaging core obtained as the ultrasound imaging core moves through a body lumen;
identifying at least one bifurcation of the body lumen from the sequence of IVUS data;
estimating a bifurcation angle between two branches, extending from a main vessel, of the body lumen, wherein estimating the bifurcation angle comprises obtaining an angiographic projection of the body lumen; and determining the bifurcation angle from the angiographic projection; and applying a geometric transformation to the IVUS data to transform at least portions of the IVUS data representing each of the two branches of the body lumen to produce a geometric alignment of the two branches according to the bifurcation angle; and
displaying the transformed IVUS data as a non-linear IVUS longitudinal view of the body lumen with the two branches displayed in the non-linear IVUS longitudinal view according to an anatomical morphology of the two branches and the main vessel.

10. The system of claim 9, wherein actions further include
determining a centerline for the IVUS data through the at least one bifurcation;
determining a centerline for the angiographic projection through the at least one bifurcation; and
aligning the centerline for the IVUS data with the centerline for the angiographic projection.

11. The system of claim 9, wherein the sequence IVUS data comprises a plurality of frames of IVUS data and wherein identifying at least one bifurcation comprises applying at least one of the frames of IVUS data to a classifier trained to identify whether a frame contains a bifurcation of a body lumen.

12. The system of claim 9, wherein the sequence IVUS data comprises a plurality of frames of IVUS data and wherein identifying at least one bifurcation comprises observing an eccentricity of a lumen of in one or more frames of the IVUS data.

* * * * *